_United States Patent_ [19]

La Russa et al.

[11] 4,046,463

[45] Sept. 6, 1977

[54] INDICATING AN ASPHERICITY OF THE CORNEA OF AN EYE

[75] Inventors: Joseph A. La Russa, Yorktown Heights; Richard C. Troutman, New York, both of N.Y.

[73] Assignee: Surgical Microsystems, Inc., New York, N.Y.

[21] Appl. No.: 489,149

[22] Filed: July 17, 1974

[51] Int. Cl.² ............................ A61B 3/10; G01B 9/00
[52] U.S. Cl. ......................................... 351/13; 356/124
[58] Field of Search ....................... 356/124, 125, 127; 351/13, 39; 240/41.35

[56] References Cited

U.S. PATENT DOCUMENTS

| | | | |
|---|---|---|---|
| 3,127,113 | 3/1964 | Tomkinson | 240/41.35 |
| 3,248,162 | 4/1966 | Knoll | 351/13 |
| 3,264,932 | 8/1966 | Hendricks | 351/39 |
| 3,542,458 | 11/1970 | Volk | 351/13 |
| 3,590,232 | 6/1971 | Sadowski | 240/2 |

Primary Examiner—John K. Corbin
Assistant Examiner—Conrad Clark
Attorney, Agent, or Firm—Leonard Weiss

[57] ABSTRACT

A circular array of twelve light sources transmit light to an eye. A spherical shape of the cornea of the eye is indicated when light reflected therefrom appears to be transmitted from twelve virtual light sources disposed along a circular path within the eye. Correspondingly, an aspherical shape of the cornea is indicated when the virtual sources appear to be disposed along an acircular path within the eye. The array may be disposed within a light reflecting groove which collects ambient light which is transmitted to the eye. A reflection of the collected light appears to be a ring of light which connects the virtual sources.

7 Claims, 9 Drawing Figures

INDICATING AN ASPHERICITY OF THE CORNEA OF AN EYE

BACKGROUND OF THE INVENTION

1. Field of the Invention

This invention is in the field of optical instrumentation and more particuarly related to apparatus for indicating and measuring an asphericity of the exterior surface of an eye.

2. Description of the Prior Art

A portion of an eye which forms the exterior surface thereof is known as a cornea. For the eye to provide normal vision, the cornea has a spherical shape, an aspherical shape being the cause of a visual defect which is known as astigmatism. Accordingly, providing an indication of the asphericity of the cornea corresponds to providing an indication of the extent of the astigmatism of the eye.

It is desirable to provide the indication of the asphericity during an adjustment of sutures used to close an incision in the cornea during ophthalmic surgery. The incision closure is typically associated with a corneal transplant or a cataract removal. It should be appreciated that an operating microscope is almost always used by a surgeon to view the incision during the ophthalmic surgery.

Additionally, during a visit of a patient to the office of an ophthamologist it is often desirable to accurately measure the asphericity of an eye of the patient. The accurate measurement of the asphericity may be required for prescribing either opthalmic spectacle lenses or contact lenses.

The asphericity is measured by apparatus sold by American Optical Company and Bausch & Lomb, Inc. under marketing designations of Ophthalmometer and Keratometer, respectively. The apparatus is typically comprised of first and second illuminated symbols which are complementary to each other.

In a typical measurement of the asphericity, the ophthalmologist positions the first symbol at one of a plurality of selected locations with respect to the patient's eye and observes a reflection therefrom of an image of the first symbol. During the observation, the second symbol is positioned to cause a reflection from the patient's eye of an image of the second symbol superimposed upon the image of the first symbol. A notation is made of the relative positions of the symbols when the superimposed images are observed. Similarly, a superimposition and a notation is made when the first symbol is moved to each of the selected locations. The asphericity may be determined from the notations.

Because the apparatus is usually bulky, it may be an obstacle to the surgeon during the ophthalmic surgery. Additionally, the positioning of the symbols is time consuming and difficult.

SUMMARY OF THE INVENTION

An object of the present invention is to provide an indication of an asphericity in the shape of the cornea of an eye.

Another object of the present invention is to provide an instrument for indicating an asphericity in the shape of the cornea of an eye where the instrument is suitable for use in conjunction with an operating microscope.

Another object of the present invention is for rapidly indicating an asphericity of the cornea of an eye.

Still another object of the present invention is to provide an instrument for measuring an asphericity in the shape of the cornea of an eye.

Another object of the present invention is to provide an instrument for rapidly measuring an asphericity in the shape of the cornea of an eye.

According to the present invention, in indicating an asphericity of a nominally spherical light reflecting object, an illuminated annulus is positioned to transmit light to said object to cause a reflection of light therefrom which appears to be transmitted from a path within said object, said path being circular in response to said object being spherical whereby a measurement of an acircularity of said path is equivalent to a measurement of said asphericity.

A first instrument in accordance with the invention may be of a small size and, in conjunction with a binocular type of operating microscope, used to rapidly indicate an asphericity of the cornea of an eye.

A second instrument in accordance with the invention may be adapted for use with a single objective microscope to provide a rapid measurement of the asphericity. The second instrument is typically used for proscribing either spectacle lenses or contact lenses for a patient.

The present invention may be utilized to provide an instrument for measuring the asphericity more accurately than apparatus known in the prior art.

Other objects, features and advantages of the present invention will become more apparent in the light of the following detailed description of preferred embodiments thereof, as illustrated in the accompanying drawing.

DESCRIPTION OF THE PREFERRED EMBODIMENT

Figure 1:
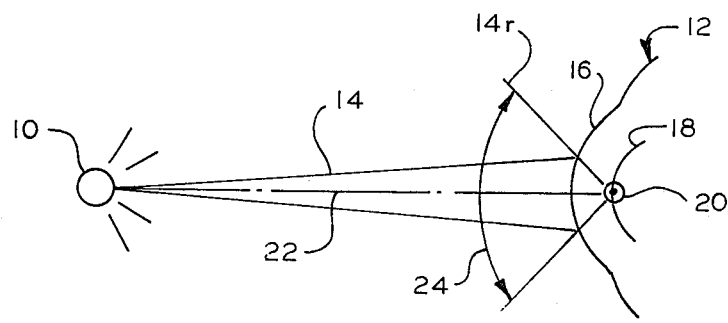
FIG. 1 is a schematic showing of light being reflected from the cornea of an eye.

Referring now to FIG. 1, a principle of the invention is exemplified by a spherical light source 10 which transmits light in the general direction of an eye 12. A portion of the light from the source 10 is transmitted along a path 14 to the cornea 16 of the eye 12.

When the cornea 16 is spherical, the light transmitted along the path 14 is reflected from the cornea 16 along a path 14r which may be extrapolated within the eye 12 to converge on a focal surface 18. Because the cornea 16 is spherical, the surface 18 is spherical. Additionally, the region of convergence on the surface 18 is a virtual light source 20 whereby the path 14r appears to an observer to be transmitted from the virtual source 20.

The surface 18 has half the radius of the cornea 16 and is concentric therewith. The sources 10, 20 and the eye 12 all have respective radii colinear with a central axis 22.

The diameters of the sources 10, 20 are in a well known ratio relationship which is given as:

$$\frac{D_2}{D_1} = \frac{\frac{R}{2}}{A}$$

where
 $D_1$ is the diameter of the source 10;
 $D_2$ is the diameter of the virtual source 20;
 R is the radius of the cornea 16; and
 A is the distance between the source 10 and a point closest thereto on the cornea 16.

Using well known algebra, the ratio relationship may be manipulated to provide a minification relationship for determining the diameter of the virtual source 20. The minification relationship is given as:

$$D_2 = \frac{D_1 R}{2A}$$

In present invention the distance between the source 10 and the cornea 16 (A) is much larger than the radius of the cornea 16 (R). Therefore, the diameter of the virtual source 20 ($D_2$) is much smaller than the diameter of the source 10 ($D_1$). Accordingly, the virtual source 20 is a minification of the source 10.

In accordance with the explanation given hereinbefore, the path 14r defines a solid angle 24 wherein the virtual source 20 is visible to the observer. It should be appreciated that the angle 24 is much larger than a corresponding solid angle defined by the path 14.

In a first embodiment of the present invention, an illuminated annulus is defined by twelve light sources mounted in a circular array around the head of an operating microscope. As explained hereinafter, when a patient is positioned for ophthalmic surgery, the operating microscope provides to a surgeon a view of twelve virtual light sources disposed within an eye of the patient along a path which nominally defines a circle. An acircularity of the path is an indication of an asphericity of the cornea of the patient's eye.

Figure 2:
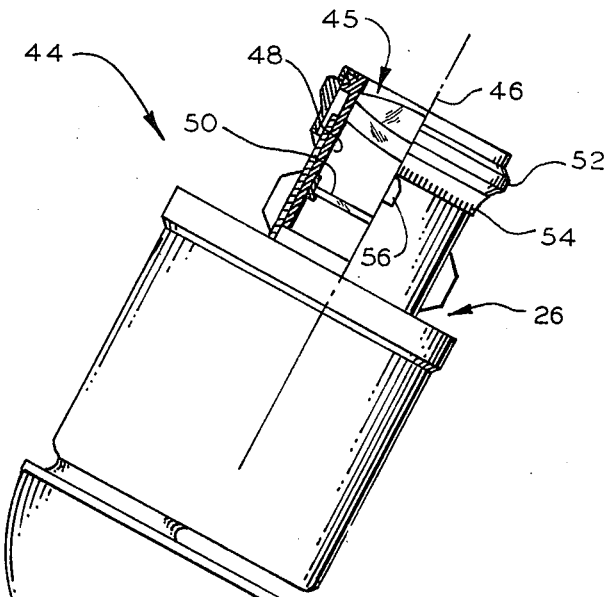
FIG. 2 is a fragmentary side elevation, with parts broken away, of a first embodiment of the present invention.
Figure 3:
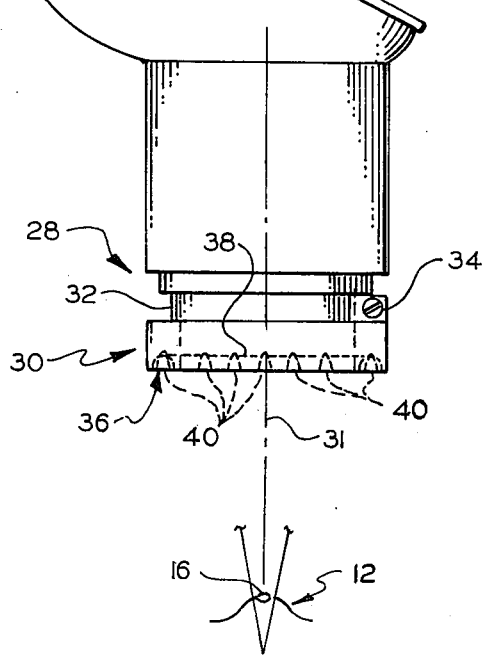
FIG. 3 is a plan view of an annular housing in the embodiment of FIG. 2.

Referring now to FIGS. 2 and 3, a view of the cornea 16 is provided to the surgeon through a binocular operating microscope having objective lenses 25a, 25b. The microscope 26 has a head 28 whereon an annular lamp housing 30 is fixedly mounted. The housing 30 has a central mechanical axis 31 which extends intermediate to the objectives 25a, 25b. In this embodiment, the housing 30 includes a clamping ring 32 which receives the head 28 and is fixedly connected thereto by a clamping screw 34. In alternative embodiments the housing 32 may be fixedly connected to the head 28 in any suitable manner.

An end 36 of the housing 30 forms a light reflecting groove 38 having a cross-section which is an arc of a circle. The groove 38 extends around the end 36 whereby the groove 38 forms a circle about a point on the axis 31. Usually, a distance of approximately six inches separates the end 36 from the eye 12 along the axis 31.

Within the groove 38 twelve lamps 40 are mounted with equal displacements between adjacent lamps whereby the lamps 40 are mounted along the circle about the axis 31. In accordance with the invention, light from the lamps 40 define an illuminated annulus which transmits light to the cornea 16. In accordance with the explanation given in connection with FIG. 1, the light from the lamps 40 is reflected from the cornea 16 whereby the view provided to the surgeon through the microscope 26 includes twelve virtual light sources 42 which are respective minifications of the lamps 40.

Figure 4:
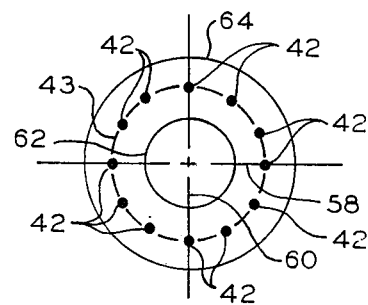
FIG. 4 is a view of a spherical cornea through a microscope in the embodiment of FIG. 2.

Referring now to FIG. 4, since the lamps 40 are mounted along the circle about the axis 31, when the cornea is spherical (causing the surface 18 to be spherical) the view includes the twelve virtual sources 42 disposed along a circular path.

Figure 5:
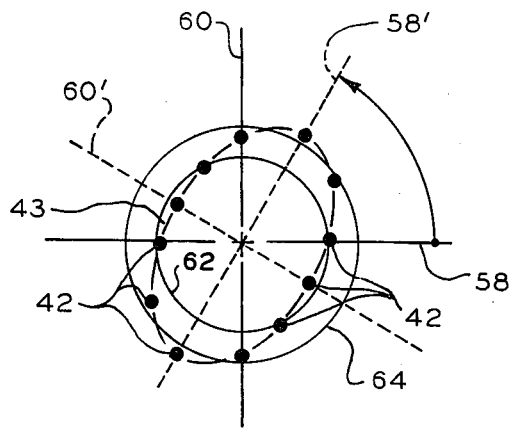
FIG. 5 is a view of an aspherical cornea through a microscope in the embodiment of FIG. 2.

Referring now to FIG. 5, when the cornea 16 is aspherical the surface 18 is aspherical whereby the view includes the twelve virtual sources 42 disposed along an acircular path. Typically, the acircular path resembles an ellipse.

Because the groove 38 is formed by a light reflecting surface, ambient light is collected therein and, according to well known optical principles, focused on a toroidal focal surface (analogous to the surface 18) having a cross-section of the groove 38. Additionally, the cross-sectional radius of the toroidal focal surface equals half of the cross-sectional radius of the groove 38.

The collected light is transmitted to the cornea 16 and is reflected therefrom. In accordance with the explanation given in connection with FIG. 1, the view additionally includes a ring of light 43 which is a minification of the toroidal focal surface. As explained hereinafter, the twelve virtual sources 42 and the ring of light 43 appear to be disposed along a path which may be compared with a rotatable reticle in a limb of the microscope 26. The comparison may be used by the surgeon in the adjustment of sutures in the cornea 16.

The microscope 26 (FIG. 2) has a limb 44 which contains the objective 25a (FIG. 3) and an eyepiece 45 which is mounted for rotation about an optical axis 46. The eyepiece 45 includes a tubular member 48 fixedly connected to a circular glass reticle 50 which is disposed within the focal plane of the objective 25a. Accordingly, the reticle 50 rotates (within the focal plane of the objective 25a) about the axis 46 when the member 48 is rotated.

A portion 52 of the eyepiece 45 extends to the outside of the limb 44 whereby the eyepiece 45 may be manually rotated.

The portion 52 has a scale 54 scribed on a portion thereof. Adjacent to the scale 54 is an index pointer 56 which is fixedly mounted on the limb 44. Therefore, a rotational position of the eyepiece 45 is indicated on the scale 54 by the pointer 56.

The reticle 50 has etched therein a pair of orthogonal lines 58, 60, an inner circle 62 and an outer circle 64. The circles 62, 64 are concentric, the centers thereof being at the intersection of the lines 58, 60 (FIGS. 4 and 5). Because the reticle 50 is in the focal plane of the objective 25a, the view through the microscope 26 is of the lines 58, 60 and the circles 62, 64 superimposed upon the cornea 16.

When the cornea 16 is spherical, the disposition of the twelve virtual sources 42 and the ring of light 43 is concentric with the circles 62, 64 (FIG. 4) and radially intermediate thereto. Conversely, when the cornea 16 is aspherical, the acircular path has portions thereof which may not be radially intermediate to the circles 62, 64 (FIG. 5).

The eyepiece 45 may be rotated to cause an alignment of the lines 58, 60 with major and minor axes, respectively, of the acircular path whereby the pointer 56 indicates on the scale 54 a rotational orientation of the major and minor axes. The indication of the orientation (and the view through the microscope 26) may be utilized to adjust sutures in the cornea 16 thereby causing the acircular path to become circular (whereby the cornea 16 becomes spherical).

In one alternative embodiment the groove 38 does not have the lamps 40 mounted therein whereby the illuminated annulus is defined by the collected ambient light and the asphericity is indicated only by the acircularity of the ring of light 43. In another alternative embodiment the illuminated annulus is defined by a lamp having a toroidal shape.

Thus, there is described hereinbefore an instrument which, in conjunction with an operating microscope, is used for indicating the asphericity of the cornea of an eye.

Figure 6:
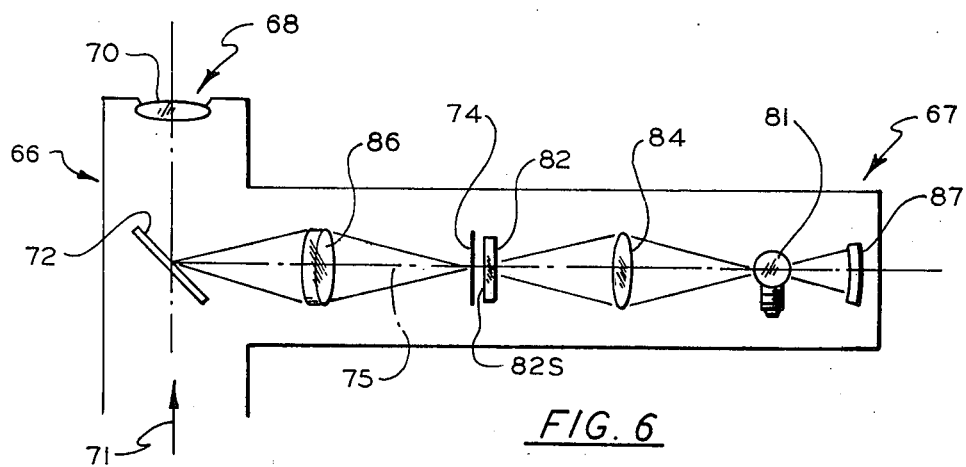
FIG. 6 is a schematic showing of a second embodiment of the present invention.
Figure 8:
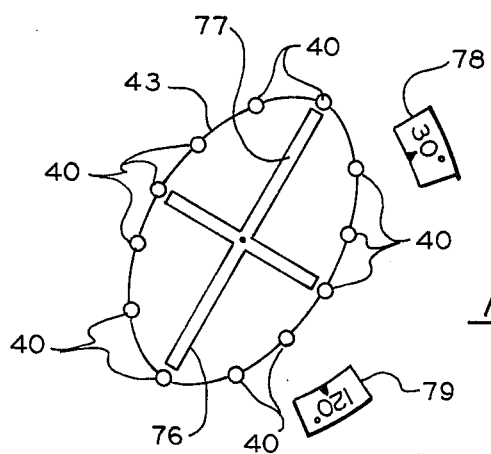
FIG. 8 is a representation of an eye viewed by an observer through a microscope in the embodiment of FIG. 6.
Figure 7:
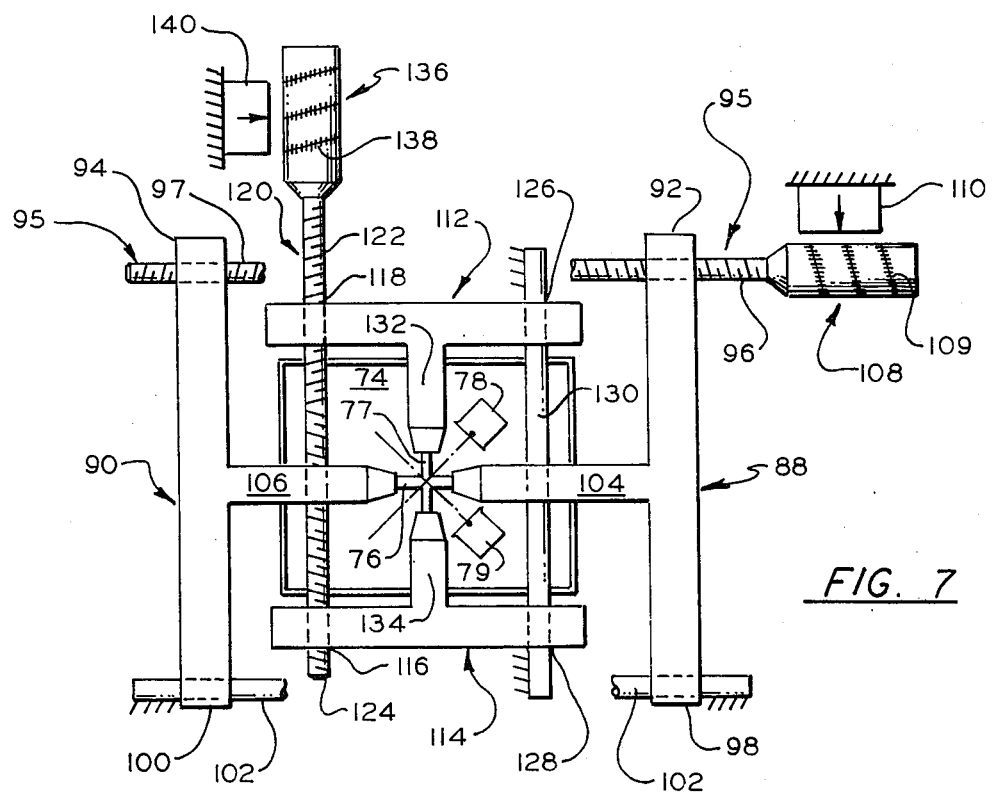
FIG. 7 is a plan view of an adjustable mask in the embodiment of FIG. 6.

It should be understood that all important measurements of the asphericity are equivalent to respective measurements of the lengths of the major and minor axes and the rotational orientation. Referring now to FIGS. 6–8, the equivalent measurements are provided in a second embodiment of the present invention where a single objective microscope 66 is positioned to provide therethrough a view of light reflected from a cornea (not shown). The microscope 66 has a head (not shown) whereon the housing 30 (FIG. 2) is mounted as described hereinbefore.

The microscope 66 has an eyepiece 68 which includes a fixedly mounted eyepiece lens 70 where there is provided (through the microscope 66) a view which is comprised of a first portion which includes the twelve virtual sources 42 and the ring of light 43 described hereinbefore. The lens 70, which collimates the view through the microscope 66, is of a type well known in the art.

To provide the first portion, approximately half of the light reflected from the cornea is transmitted in a direction indicated by an arrow 71 through a fixedly mounted beam splitter 72. The half of the light from the cornea which is not transmitted through the beam splitter 72 is reflected therefrom and lost. The beam splitter 72 may be of any suitable type and, in alternative embodiments, may reflect and transmit light in any desired proportions.

The microscope 66 includes a reticle projecting and measuring system 67 which comprises an opaque reticle lens 74 having a lens axis which is in substantial alignment with an optical axis 75; the reticle 74 is rotatable about the axis 75. The reticle 74 carries a pattern comprised of mutually orthogonal non-opaque segments 76, 77 which form an intersection with the axis 75 (FIG. 7).

The pattern additionally includes windows 78, 79 which have a known radial displacement from the axis 75. The windows 78, 79 have an angular displacement therebetween of 90° (about the axis 75).

As explained hereinafter, a second portion of the view through the microscope 66 includes an image of the segments 76, 77 formed by light which passes therethrough. The second portion additionally includes an image of a portion of a scale which is formed by light which passes through the windows 78, 79.

The second portion is transmitted through the lens 70 whereby the view through the microscope 66 is comprised of the second portion superimposed upon the first portion.

To provide the second portion, a lamp 81 is mounted to transmit light to an opal glass diffuser 82 fixedly mounted adjacent to the reticle 74. The light from the lamp 81 is transmitted through a fixedly mounted condensing lens 84 which has an optical axis along the axis 75. Light from the lamp 81 is focused by the lens 84 upon the diffuser 82. The diffuser 82 diffuses the light focused thereon thereby providing a uniform illumination of the reticle 74.

Because of the illumination of the reticle 74, a transmitted portion of light passes through the segments 76, 77 and the windows 78, 79 to a fixedly mounted projection lens 86 which has an optical axis along the axis 75. All of the illumination passing through the segments 76, 77 and the windows 78, 79 is gathered, projected and focused in the focal plane of the objective of the microscope 66 by the lens 86 via a reflection from the beam splitter 72. Because the illumination passing through the segments 76, 77 and the windows 78, 79 is in the focal plane of the objective of the microscope 66, the second portion, superimposed upon the first portion, is transmitted through the lens 70.

One portion of the light from the lamp 81 is directly transmitted to the diffuser 82 while another portion is transmitted thereto via a fixedly mounted reimaging mirror 87 which has an optical axis along the axis 75. It should be appreciated that the mirror 87 reimages the other portion past the lamp 81 to the diffuser 82 via the lens 84. Because of the reimaging, the diffuser 82 receives approximately twice the amount of light which is directly transmitted thereto. It should be understood that diffusers, condensing lenses and reimaging mirrors are all well known in the art.

To provide an indication of a rotational position of the reticle 74, the diffuser 82 carries a scale on a side 82S thereof. The scale is disposed circumferentially at the known radial displacement (of the windows 78, 79 from the axis 75). Accordingly, the second portion includes an image of a portion of the scale which is formed by the light transmitted through the windows 78, 79 (FIG. 8).

Since the reticle 74 is rotatably mounted and the diffuser 82 is fixedly mounted, the image of the portion of the scale provides an indication of a rotational position of the reticle 74. Because of the 90 degree displacement between the windows 78, 79, when the reticle 74 is rotated to cause an alignment of the image of the segment 76 with the major axis and an alignment of the segment 77 with the minor axis, or vice versa, the image of the portion of the scale indicates respective rotational orientations of the major and minor axes.

The reticle 74 includes a variable mask comprised of a pair of members 88, 90 with respective ends 92, 94 which have opposite hand threaded holes therethrough. The holes in the ends 92, 94 are aligned to receive a shaft 95 having portions 96, 97 which are opposite hand threaded.

Additionally, the members 88, 90 have ends 98, 100, respectively, each with a smooth hole therethrough. The ends 98, 100 have slideably mounted therein a shaft 102 which is fixedly connected at the ends thereof to the barrel (not shown) of the microscope 66.

Because of the opposite hand threading and the slideable mounting, the members 88, 90 are moveable (within the span of the ends of the shaft 102) in the familiar manner of jaws of a clamp on a roller skate. Accordingly, the members 88, 90 advance respectively equal distances in the direction of the intersection of the segments 76, 77 in response to a clockwise rotation of the shaft 95. Conversely, the members 88, 90 withdraw respectively equal distances from the intersection in response to a counter clockwise rotation of the shaft 95.

The members 88, 90 include mask portions 104, 106, respectively. The mask portions 104, 106 extend over respective ends of the segment 76 in accordance with the rotation of the shaft 95. Hence, the mask portions 104, 106 selectively occlude the segment 76 whereby an image of an unoccluded portion of the segment 76 (included in the second portion) is in accordance with a rotational position of the shaft 95.

The shaft 95 includes an end 108 having a scale 109 scribed thereon. Adjacent to the end 108 is an index pointer 110 which is fixedly mounted on the microscope 66. Therefore, the length of the unoccluded portion of the segment 76 is indicated on the scale 109 by the pointer 110.

The variable mask additionally includes a pair of members 112, 114 with respective ends 116, 118 which have opposite hand threaded holes therethrough. The holes in the ends 116, 118 are aligned to receive a shaft 120 having portions 122, 124 which are opposite hand threaded.

Additionally, the members 112, 114 have ends 126, 128, respectively, each having a smooth hole therethrough. The ends 126, 128 have slidebly mounted therein a shaft 130 which is fixedly connected at the ends thereof to the barrel of microscope 66.

In a manner similar to the members 88, 90 described hereinbefore, the members 112, 114 advance and withdraw in response to respective clockwise and counterclockwise rotations of the shaft 120.

The members 112, 114 include mask portions 132, 134, respectively, which are similar to the mask portions 104, 106. The mask portions 132, 134 extend over respective ends of the segment 77 in accordance with the rotation of the shaft 120. Hence, the mask portions 132, 134 selectively occlude the segment 77 whereby an image of an unoccluded portion of the segment 77 (included in the second portion) is in accordance with a rotational position of the shaft 120.

The shaft 120 includes an end 136 having a scale 138 scribed thereon. Adjacent to the end 136 is an index pointer 140 which is fixedly mounted on the microscope 66. Therefore, the length of the unoccluded portion of the segment 77 is indicated on the scale 138 by the pointer 140.

In accordance with the explanation given hereinbefore, when the image of the segment 76 is aligned with the major axis and the image of the segment 77 is aligned with the minor axis, or vice versa, the selective occlusion may cause the length of the image of the segments 76, 77 to equal the lengths of the major and minor axes, respectively of the acircular path. Therefore, the selective occlusion may be utilized to provide indications on the scales 109, 138 of the respective lengths of the major and minor axes. It should be appreciated that degree of astigmatism is associated with the relative lengths of the major and minor axes.

Thus there is described hereinbefore an instrument for providing measurements of the asphericity of a cornea.

Figure 9:
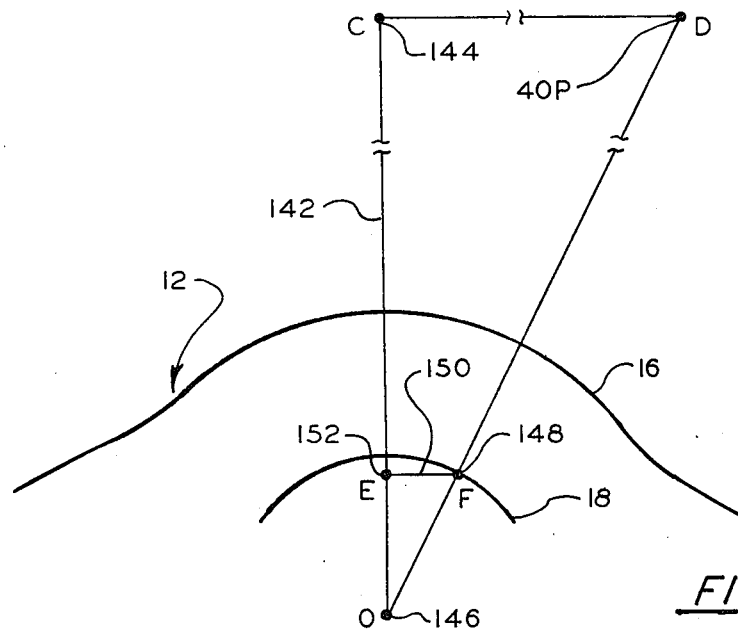
FIG. 9 is a schematic showing of a point source which transmits light to a cornea.

Referring now to FIG. 9, a feature common to both embodiments is exemplified by a microscope having an optical axis 142 which intersects the eye 21. The axis 142 extends to a head of the microscope at a point 144 which is six inches from the eye 12. Additionally the cornea 6 has a radius of curvature equal to 0.32 inches. Therefore, the point 144 is 6.32 inches from a center of curvature 146 of the cornea 16.

Light is directed towards the eye 12 from a point source of light 40P which is disposed 1.625 inches from the point 144 on a line which is perpendicular to the axis 142.

In accordance with the teachings of the present invention, light from the point source 40P appears to be reflected from a virtual light source 148. The virtual source 148 is at an intersection of the surface 18 with a line connecting the center of curvature 146 to the source 40P.

A first triangle includes a line 150 which intersects the virtual source 148 and perpendicularly intersects the axis 142 at a point 152. The first triangle additionally includes lines connecting the center of curvature 146 to the source 148 and the point 152. According to well known trigonometry, the first triangle is similar to a second triangle which includes a line which connects the point source 40P to the point 144 and lines connecting the center of curvature 146 to the point source 40P and the point 144.

Because of the similarity of the triangles, the distance of the virtual source 148 from the point 152 is in accordance with a similarity relationship which is given as:

$$EF = \frac{(CD)(OE)}{(OC)}$$

where EF is the distance of the virtual source 148 from the point 152;

CD is 1.625 inches, the distance of the point source 40P from the point 144;

OE is approximately equal to 0.15 inches, the distance of the center of curvature 146 from the point 152; and OC is 6.32 inches, the distance of the point 144 from the center of curvature 146.

Therefore, EF = 0.04 inches.

Accordingly, the distance of the source 148 from the point 152 is a minification of the distance of the point source 40P to the point 144. Because of the minification, a small movement of the source 40P, towards and away from the point 144, causes substantially no change of the distance (EF) of the virtual source 148 from the point 152. However, a small change in the radius of curvature of the cornea 16 causes a corresponding change in the radius of the sphere 18 thereby causing a substantial change of the distance of the virtual source 148 from the point 152.

Although the invention has been shown and described with respect to preferred embodiments thereof, it should be understood by those skilled in the art that various changes and omissions in the form and detail thereof may be made therein without departing from the spirit and the scope of the invention.

Having thus described typical embodiments of our invention, that which we claim as new and desire to secure by Letters of Patent of the United States is:

1. Apparatus for providing an indication of an asphericity of the cornea of an eye viewed through a binocular microscope of the type used for ophthalmic surgery, comprising:

a housing adapted for connection around the head of said microscope;

a plurality of light sources connected to said housing along a circle around said head, light from said sources being transmitted to said eye; and a rotatable reticle disposed within the focal plane of an objective of said microscope, said reticle having a pair of concentric circles whereby said asphericity is indicated by said view being of a reflection of said sources disposed along an acircular path having a portion which is not intermediate to said concentric circles.

2. Apparatus according to claim 1 additionally comprising means for providing an indication of a rotational position of said reticle.

3. Apparatus for providing an indication of an asphericity of the cornea of an eye viewed through a single objective microscope, comprising:

an annular housing connected around the head of said microscope;

a plurality of light sources connected to said housing along a circle around the head of said microscope;

a generally opaque reticle which has a pair of orthogonal intersecting non-opaque segments;

means for illuminating said reticle;

means for occluding selected portions of said segments;

means for focussing, in the focal plane of said objective, light passing through said reticle whereby an image of unoccluded portions of said reticle is viewed through said microscope; and means for rotating said reticle about the intersection of said segments.

4. Apparatus according to claim 3 additionally comprising means for providing an indication of lengths of unoccluded portions of said segments.

5. Apparatus according to claim 3 wherein said reticle has a pair of non-opaque windows having a known displacement from the intersection of said segments, said windows having an angular displacement therebetween substantially equal to ninety degrees, said illuminating means additionally comprising a scale disposed circumferentially at said known displacement whereby an image of a portion of said scale is formed by light passing through said windows.

6. Apparatus according to claim 3 wherein said housing includes a circular light reflecting groove, said light sources being disposed within said groove.

7. Apparatus according to claim 3 wherein said groove has a cross section which is an arc of a circle.

* * * * *